(12) United States Patent
Townsend et al.

(10) Patent No.: US 11,116,310 B2
(45) Date of Patent: Sep. 14, 2021

(54) ORAL CARE IMPLEMENT

(71) Applicants: Lori Townsend, Irvine, CA (US);
Raymond Szeto, Boston, MA (US)

(72) Inventors: Lori Townsend, Irvine, CA (US);
Raymond Szeto, Boston, MA (US)

( * ) Notice: Subject to any disclaimer, the term of this patent is extended or adjusted under 35 U.S.C. 154(b) by 434 days.

(21) Appl. No.: 15/770,813

(22) PCT Filed: Oct. 26, 2016

(86) PCT No.: PCT/US2016/058936
§ 371 (c)(1),
(2) Date: Apr. 25, 2018

(87) PCT Pub. No.: WO2017/075097
PCT Pub. Date: May 4, 2017

(65) Prior Publication Data
US 2020/0237091 A1     Jul. 30, 2020

Related U.S. Application Data

(60) Provisional application No. 62/246,571, filed on Oct. 26, 2015, provisional application No. 62/314,985, filed on Mar. 29, 2016.

(51) Int. Cl.
*A46B 15/00* (2006.01)
*A46B 17/08* (2006.01)
*A61B 17/24* (2006.01)

(52) U.S. Cl.
CPC .......... *A46B 15/0081* (2013.01); *A46B 17/08* (2013.01); *A61B 17/244* (2013.01)

(58) Field of Classification Search
CPC .............. A61B 17/244; A46B 15/0081; A46B 2200/1026; A46B 2200/1066; A46B 15/0022; A61C 17/22; A61C 17/32; A61C 17/34; B29L 2031/425
See application file for complete search history.

(56) References Cited

U.S. PATENT DOCUMENTS

| | | | | |
|---|---|---|---|---|
| 5,165,131 A | * | 11/1992 | Staar ....................... | A46B 15/00 15/22.1 |
| 5,735,864 A | * | 4/1998 | Heisinger, Jr. ....... | A61B 17/244 15/111 |
| 5,792,159 A | * | 8/1998 | Amin ................... | A61B 17/244 15/236.06 |
| 5,810,856 A | * | 9/1998 | Tveras ................. | A61B 17/244 606/161 |

(Continued)

FOREIGN PATENT DOCUMENTS

| | | |
|---|---|---|
| CN | 1711045 A | 10/2003 |
| CN | 1809301 A | 6/2004 |

(Continued)

*Primary Examiner* — Phong Son H Dang
(74) *Attorney, Agent, or Firm* — Sterne, Kessler, Goldstein & Fox P.L.L.C.

(57) ABSTRACT

A oral care implement for cleaning soft oral tissue of the mouth, such as the tongue. The oral care implement includes a handle, an intermediary region, and a cleaning region. The cleaning regions include a plurality of collecting bases for collecting debris from the oral tissue. The collecting bases may include multiple protrusions that extend from the collecting bases that remove debris from the user's soft oral tissue.

20 Claims, 6 Drawing Sheets

(56) References Cited

U.S. PATENT DOCUMENTS

| | | | | |
|---|---|---|---|---|
| 5,984,935 | A | * | 11/1999 | Welt .................. A61B 17/244 606/161 |
| 6,131,228 | A | * | 10/2000 | Chen .................. A46B 9/04 15/160 |
| D447,238 | S | * | 8/2001 | Tang ........................ D24/147 |
| 8,202,286 | B1 | * | 6/2012 | Suzman ............... A61B 17/244 606/161 |
| 8,745,804 | B2 | | 6/2014 | Jaksha |
| 9,597,496 | B1 | * | 3/2017 | Johansson .......... A46B 15/0022 |
| D842,472 | S | * | 3/2019 | Townsend .................. D24/147 |
| 2003/0115699 | A1 | * | 6/2003 | Wagstaff ............ A46B 15/0055 15/111 |
| 2005/0069372 | A1 | | 3/2005 | Hohlbein et al. |
| 2006/0010628 | A1 | | 1/2006 | Moskovich |
| 2006/0052805 | A1 | * | 3/2006 | Cwik .................. A61B 17/244 606/161 |
| 2011/0047735 | A1 | * | 3/2011 | Jaksha ............... A46B 15/0055 15/167.1 |
| 2011/0152909 | A1 | | 6/2011 | Jimenez et al. |
| 2011/0289707 | A1 | * | 12/2011 | Schaefer ................ A61N 1/322 15/105 |
| 2012/0322023 | A1 | * | 12/2012 | Hohlbein ........... A61B 10/0051 433/27 |
| 2014/0325777 | A1 | | 11/2014 | Chang |
| 2015/0000064 | A1 | * | 1/2015 | Moskovich .......... A46B 5/0029 15/105 |

FOREIGN PATENT DOCUMENTS

| | | |
|---|---|---|
| CN | 101039630 A | 8/2005 |
| CN | 102883669 A | 5/2011 |
| EP | 2 384 707 A1 | 11/2011 |
| GB | 2 355 202 A | 4/2001 |
| JP | H 5-504708 A | 7/1993 |
| JP | 2000-325367 A | 5/1999 |
| JP | 2001-457 A | 1/2001 |
| JP | 2001-161720 A | 6/2001 |
| JP | 2005-342489 A | 12/2005 |
| JP | 2010-124904 A | 6/2010 |
| JP | 3164878 U | 12/2010 |
| JP | 2012-95869 A | 5/2012 |
| JP | 2015-73586 A | 4/2015 |
| WO | WO 98/08458 A2 | 3/1998 |

* cited by examiner

ORAL CARE IMPLEMENT

CROSS REFERENCE TO RELATED APPLICATIONS

This application claims the benefit of provisional application No. 62/246,571, filed Oct. 26, 2015, design application No. 29/562,504 filed Apr. 26, 2016, and provisional application No. 62/314,985, filed Mar. 29, 2016, all of which are incorporated by reference herein in their entireties.

BACKGROUND

A major source of halitosis (bad breadth) is microbial flora that grows on soft oral tissues, such as the tongue, the insides of the cheek, and the gums. These microbes, as well as byproducts emitted by these microbes and the decay of food deposits and debris, contribute to bad breadth. For simplicity, we will use the term debris to collectively refer to these contributors of halitosis. Most people brush their teeth with a toothbrush and some even floss their teeth. However, brushing and flossing alone cannot effectively remove microbes on the soft oral tissues.

The present disclosure relates generally to oral care implements and devices, and more specifically it relates to a cleaner for cleaning oral tissues such as the tongue.

SUMMARY

The present disclosure generally relates to an oral care implement for cleaning soft oral tissue. In some embodiments, the oral care implement includes a handle, a head disposed on the handle, collecting bases disposed on the head, and protrusions that extend from each base. Each protrusion has a single radius of curvature in the longitudinal direction. The radius of curvature of the protrusions on one of the bases is greater than the radius of curvature of the protrusions on the other base. A user may grip the handle in order to move the tissue cleanser and clean the soft oral tissue of a mouth.

The collecting bases are formed in a number of different shapes. In some embodiments, the collecting bases are formed in rows that extend perpendicular to the longitudinal direction of the handle. In some embodiments, the collecting bases are formed in rows that curve away from the handle in opposing directions. In some embodiments, the collecting bases are formed in concentric curves.

In some embodiments, the protrusions have a substantially triangular saw-tooth shape, and wherein a free end of the protrusions forms the apex of a triangle. The protrusions of each base may be offset from the protrusions of the other bases such that when viewed along the longitudinal axis of the handle, protrusions on one base are visible between protrusions on another base.

In some embodiments, a bottom surface of each collecting base has a convex curve such that protrusions at the center of the base are lower than protrusions at the periphery of the base.

In some embodiments, a collecting channel may be disposed between adjacent rows of collecting bases for collecting debris dislodged by the protrusions. The depth of the collecting channel may vary along the axis the head. The depth of the collecting channel is different near a periphery of the collecting channel than the depth of the collecting channel is near a center.

In some embodiments, the oral care implement may be a toothbrush with a handle and a head connected to the handle. The head may have a first face and a second face opposite to the first face. Bristles may extend from the first face of the head and collecting bases may project from the second face of the head and extend the entire width of the second face. A plurality of protrusions may extend from each base. In some embodiments, the radius of curvature of the protrusions on a base is greater than the radius of curvature of the protrusions on another base.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION

Figure 1:
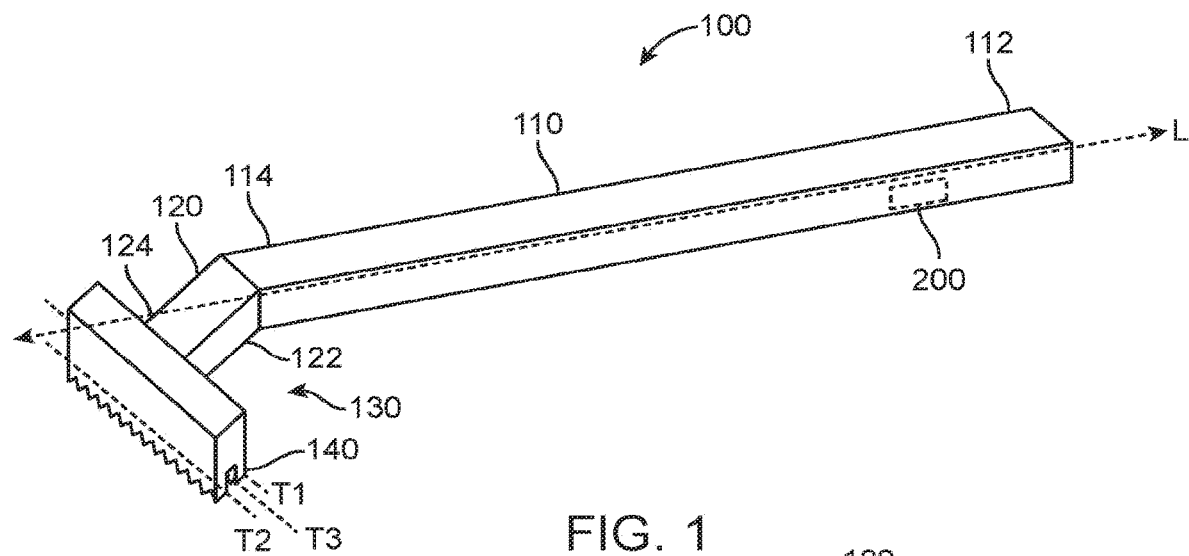
FIG. 1 illustrates a top front perspective view of an oral care implement according to an embodiment.

The present invention will now be described in detail with reference to embodiments thereof as illustrated in the accompanying drawings. References to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

This disclosure is discussed in terms of a tongue cleaner and a toothbrush, but could be in the form of other oral care implements such as a tissue cleaning lollipop. Further, it is to be understood that other embodiments may be utilized and structure and functional modifications may be made without departing from the scope of the present disclosure.

Turning now descriptively to the drawings, in which similar reference characters denote similar elements throughout the several views, the figures illustrate a handle and a cleaning region, wherein the cleaning region exhibit one or more of the elements described herein.

FIG. 1 illustrates an oral care implement, such as a tongue cleaner 100, for cleaning the soft oral tissue of a mouth. Such soft oral tissue may include the tongue, gums (gingivae), palate, buccal mucosa (lip and cheek lining), and floor of the mouth. Tongue cleaner 100 may include a handle 110, an intermediary region (neck) 120, and a tissue cleanser (head) 130.

Handle 110 may have a longitudinal axis L and may provide the user a grip to allow the user to manipulate tongue cleaner 100 and to move tissue cleanser 130 around the user's mouth in order to clean the soft oral tissue. Handle 110 may have a variety of different shapes, a variety of different constructions, and be fabricated from a variety of different materials to enhance the user's experience.

Intermediary region 120 connects handle 110 to tissue cleanser 130. Intermediary region 120 may extend tissue cleanser 130 below the longitudinal axis of handle 110. Intermediary region 120 may form an obtuse angle with handle 110, thereby placing tissue cleanser 130 below the longitudinal axis of handle 110. This extension may allow for varying the angle of contact between tissue cleanser 130 and the surface to be cleaned (e.g., tongue). For example, if the tongue exhibits a concave shape during cleaning, intermediary region 120 helps provide a better contact between tissue cleanser 130 and the tongue. Tissue cleanser 130 may form a plane that is substantially parallel to the plane formed by handle 110. Alternatively, intermediary region 120 may form an acute angle with handle 110. In other embodiments, tissue cleanser 130 may be modified such that it does not form a plane that is substantially parallel to the plane formed by handle 110, while still allowing tissue cleanser 130 to substantially maintain contact with the oral tissue.

Tissue cleanser 130 illustrated in FIG. 1 is wider than the width of handle 110 or the intermediary region 120 and may extend in a direction perpendicular to the longitudinal axis L of handle 110, thus giving tongue cleaner 100 a "T" shape. Alternatively, tissue cleanser 130 may be the same width as handle 110 or intermediary region 120, or may be narrower than handle 110 or intermediary region 120. Tissue cleanser 130 may extend away from handle 110 at an angle off the longitudinal axis L or tissue cleanser 130 may curve away from longitudinal axis L. The width of tissue cleanser 130 may be between 3 mm and 50 mm. In some embodiments, the width of tissue cleanser 130 may be about 25 mm. In other embodiments, the width of tissue cleanser 130 may be about 5 mm. The small width of tissue cleanser 130 may allow for greater maneuverability within the user's mouth, ease of use for users with small mouths, and reduce the likelihood of eliciting a pharyngeal reflex or laryngeal spasm during use.

Handle 110 illustrated in FIG. 1 is a straight rod, however, handle 110 and intermediary region 120, may have a variety of different sizes, shapes (e.g., round, curved, flat, etc.), or finishes (e.g., smooth, ridged, textured, matted, knurled recessed, etc.). Handle 110 may be any shape configured to permit the user to grip, control and/or guide tongue cleaner 100 in the user's mouth. Tongue cleaner 100 may be configured such that generally, when tongue cleaner 100 is in use, the user guides handle 110 substantially in a direction parallel to handle 110's longitudinal axis L.

Handle 110, intermediary region 120, and tissue cleanser 130 may each be made of any suitable material, such as, polymers (e.g., plastic), metal, ceramic, silica, crystalline solids, amorphous solids (e.g., glass), organic based materials (e.g., wood), and so forth. Handle 110, intermediary region 120, and tissue cleanser 130 may be fabricated from the same material or from different materials. In some embodiments, the material is polypropylene with a Shore hardness between Shore A 0 and Shore D 100. The material may also comprise polypropylenes with different hardness.

Handle 110 may have a proximal end 112 and a distal end 114 and intermediary region 120 may have a proximal end 122 and a distal end 124. Distal end 114 of handle 110 may be mechanically coupled to proximal end 122 of intermediary region 120. Distal end 124 of intermediary region 120 may be mechanically coupled to tissue cleanser 130. Thus, handle 110 may be indirectly mechanically coupled to tissue cleanser 130. In some embodiments, handle 110 may be directly mechanically coupled to tissue cleanser 130 without intermediary region 120. Either proximal end 112 or distal end 114 of handle 110 may be configured to be mechanically coupled to tissue cleanser 130. Tongue cleaner 100 may integral, monolithic, or constructed of multiple separate detachably inter-connectable components, enabling tissue cleanser 130 to be disposable after one or more uses.

Figure 2:
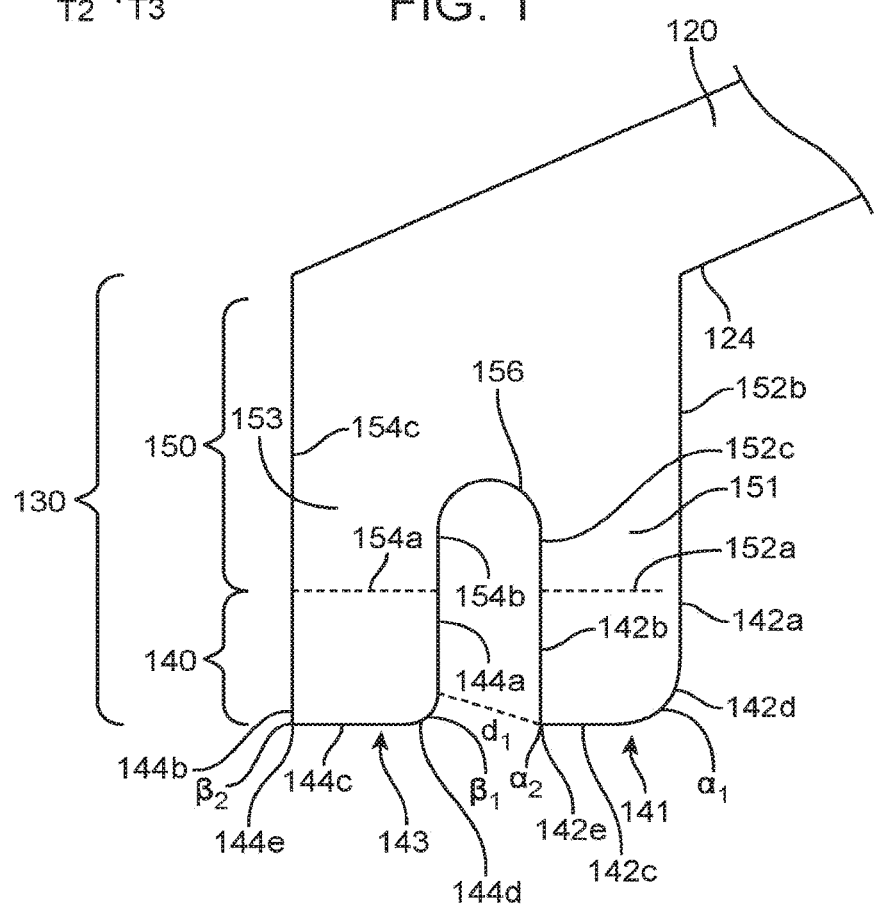
FIG. 2 illustrates a side view of a neck and a cleaning region of an oral care implement according to an embodiment.

FIG. 2 illustrates a side view of tissue cleanser 130 of tongue cleaner 100. Tissue cleanser 130 includes a cleaning region 140 and a collecting region 150. Cleaning region 140 is configured to loosen debris from the oral tissue while collecting region 150 is configured to remove and collect the loosen debris from cleaning region 140. Collecting region 150 may have multiple collecting bases. Collecting bases may have a variety of different shapes, such as, concentric closed curves, polygons, rows, blades, and the like. Collecting bases may be aligned sequentially and/or serially along longitudinal axis L.

According to one embodiment, collecting region 150 may have two bases, a first collecting base 151, also referred to as a leading base 151, and a second collecting base 153, also referred to as a trailing base 153. Leading base 151 is proximal to handle 110 and is mechanically coupled to trailing base 153, which is distal to handle 110. The terminology leading base 151 and trailing base 153 refer to which base 151 is in front of the other base when tongue cleaner 100 is in use and the user pulls or drags tongue cleaner 100, such as, from the back of the tongue to the front of the tongue in a direction parallel to handle 110's longitudinal axis L. However, the present disclosure is not so limited. The user may move tongue cleaner 100 in various directions (i.e., forward, backward, left, right, angled, and the like) to clean the soft oral tissue.

Leading base 151 supports and is mechanically coupled to a first row of protrusions 141. First row of protrusions 141 may have a corrugated surface, or in other words, first row of protrusions 141 may include multiple protrusions 141 (e.g., teeth) that project downward from a bottom surface 152a from leading base 151. Leading base 151 may have a transverse axis T1.

Trailing base 153 supports and is mechanically coupled to a second row of protrusions 143. Second row of protrusions 143 may have a corrugated surface, or in other words, second row of protrusions 143 may include multiple protrusions 143 (e.g., teeth) that project downward from a bottom surface 154a from trailing base 153. Collecting base 153 may have a transverse axis T2.

Transverse axis T1 and transverse axis T2, when transposed onto the plane containing longitudinal axis L, is substantially orthogonal to longitudinal axis L. As illustrated in FIG. 2, the axes T1 and T2 are substantially parallel to each other although neither T1 nor T2 necessarily reside in the same spatial plane as longitudinal axis L.

Leading base 151 has two surfaces that are substantially parallel to axis T1, a leading base first surface 152b and a leading base second surface 152c. Trailing base 153 has two surfaces that are substantially parallel to axis T2, a trailing base first surface 154b and a trailing base second surface 154c.

Leading base 151 and leading row protrusions 141 may be proximal to the handle compared to trailing base 153 and trailing row protrusions 143. Protrusions 141 and 143 are part of cleaning region 140 which loosens oral debris from the soft oral tissue. Bases 151 and 153 are considered part of the collecting region 150 which collects the oral debris loosened from the soft oral tissue.

Figure 3:
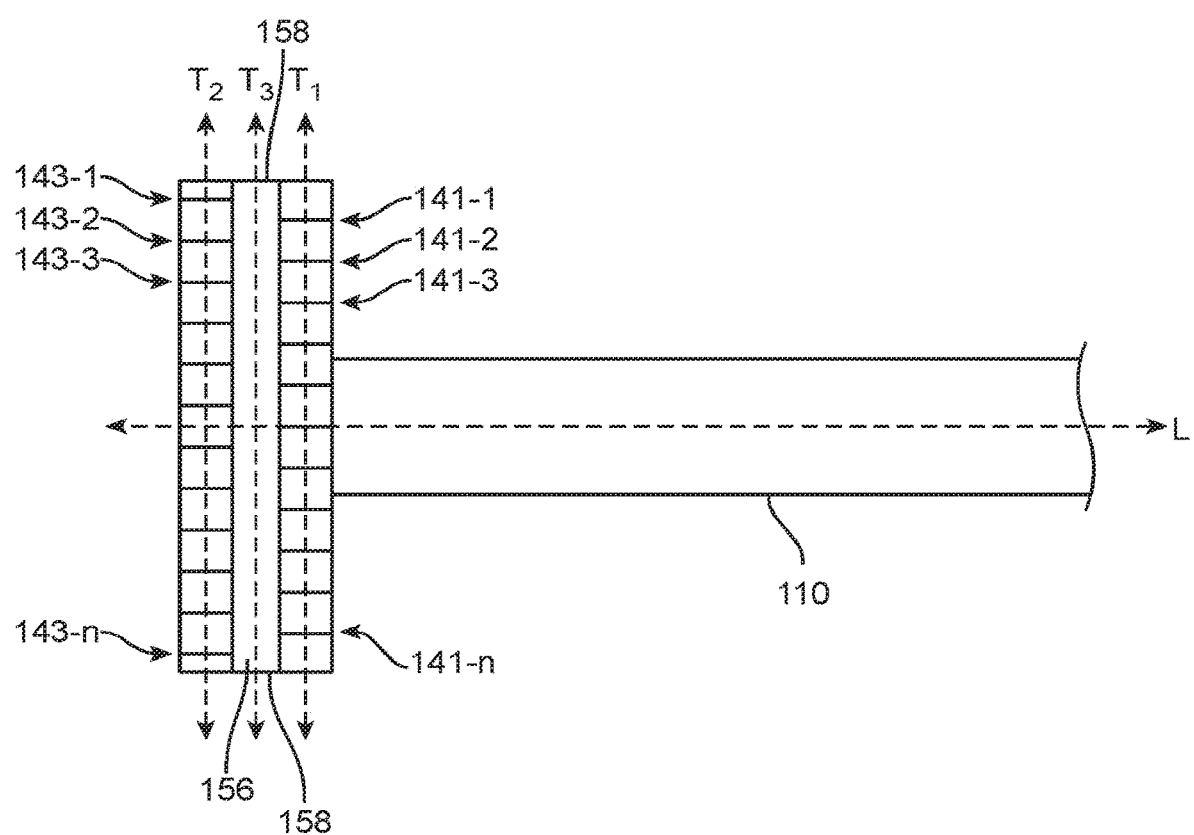
FIG. 3 illustrates a bottom view of an oral care implement according to an embodiment.

FIG. 3 illustrates a bottom view of leading row protrusions 141, which are individually referenced as 141-1 through 141-n, and trailing row protrusions 143, which are individually referenced as 143-1 through 143-n. Each leading row of protrusion 141-1 through 141-n may have three surfaces, which are illustrated in FIG. 2, a leading row protrusion first surface 142a, a leading row protrusion second surface 142b, and a leading row protrusion contact surface 142c. Leading row protrusion first surface 142a meets leading row protrusion contact surface 142c to form a leading row protrusion first contact edge 142d. Leading row protrusion first contact edge 142d may have a radius of curvature alpha1. For example, alpha1 may be between 100 microns and 500 microns. In some embodiments, leading row protrusion first contact edge 142d may be orthogonal. Alternatively, leading row protrusion first contact edge 142d may not have a single radius of curvature, but instead, may have multiple curves, each with a different radii of curvature, such as a swoosh shape. Further, leading row protrusion first contact edge 142d may have an asymptotic curve, sinusoidal curve, polynomial curve, exponential curve, logarithmic curve, and the like. Leading row protrusion first surface 142a may be continuous with leading base first surface 152b, with the angle formed by the two planes being 180 degrees, although in some embodiments, the angle may be greater than or less than 180 degrees. The surface of leading row protrusion first surface 142a and the surface of leading row protrusion second surface 142b may be parallel planes except for the curve of leading row protrusion first contact edge 142d.

Leading row protrusion second surface 142b meets leading row protrusion contact surface 142c to form a leading row protrusion second contact edge 142e, wherein the angle formed by the two surfaces is substantially orthogonal. In some embodiments, leading row protrusion second contact edge 142e is not orthogonal. For example, alpha2 may be less than or equal to 500 microns. Alternatively, leading row protrusion second contact edge 142e may not have a single radius of curvature, but instead, may have multiple curves, each with a different radii of curvature, such as a swoosh shape. Further, leading row protrusion second contact edge 142e may have an asymptotic curve, sinusoidal curve, polynomial curve, exponential curve, logarithmic curve, and the like. Leading row protrusion second surface 142b is continuous with leading base second surface 152c, with the angle formed by the two planes being 180 degrees, although in some embodiments, the angle may be greater than or less than 180 degrees.

Each trailing row protrusion 143-1 through 143-n may have three surfaces, which are illustrated in FIG. 2, a trailing row protrusion first surface 144a, a trailing row protrusion second surface 144b, and a trailing row protrusion contact surface 144c. Trailing row protrusion first surface 144a meets trailing row protrusion contact surface 144c to form a trailing row protrusion first contact edge 144d. Trailing row protrusion first contact edge 144d may have a radius of curvature beta1. For example, beta1 may be less than or equal to 500 microns. In some embodiments, trailing row protrusion first contact edge 144d may be orthogonal. Alternatively, trailing row protrusion first contact edge 144d may not have a single radius of curvature, but instead, may have include multiple curves, each with a different radii of curvature, such as a swoosh shape. Further, trailing row protrusion first contact edge 144d may have an asymptotic curve, sinusoidal curve, polynomial curve, exponential curve, logarithmic curve, and the like. Trailing row protrusion first surface 144a is continuous with trailing base first surface 154b, with the angle formed by the two planes being 180 degrees, although in some embodiments, the angle may be greater than or less than 180 degrees. The surface of trailing row protrusion first surface 144a and the surface of trailing row protrusion second surface 144b may be parallel planes except for the curve of trailing row first contact edge 144d.

Trailing row protrusion second surface 144b meets trailing row protrusion contact surface 144c to form a trailing row protrusion second contact edge 144e, wherein the angle formed by the two surfaces is substantially orthogonal. In some embodiments, trailing row protrusion second contact edge 144e is not orthogonal. For example, beta2 may be less than or equal to 500 microns. Alternatively, trailing row protrusion second contact edge 144e may not have a single radius of curvature, but instead, may have include multiple curves, each with a different radii of curvature, such as a swoosh shape. Further, trailing row protrusion second contact edge 144e may have an asymptotic curve, sinusoidal curve, polynomial curve, exponential curve, logarithmic curve, and the like. Trailing row protrusion second surface 144b is continuous with trailing base second surface 154c, with the angle formed by the two planes being 180 degrees, although in some embodiments, the angle may be greater than or less than 180 degrees.

In some embodiments, radius of curvature alpha1 of leading row protrusions 141 is greater than radius of curvature beta1 of trailing row protrusions 143. Since alpha1 has a greater radius of curvature, protrusions 141 feel smoother against the tongue of the user while the user pulls or drags tongue cleaner 100 along the tongue. Beta1 may have a smaller radius of curvature or even an orthogonal edge which supplies a better cleaning surface. The larger radius of curvature alpha1 of the leading row protrusions 141 partially desensitizes the tongue and helps reduce the irritation caused by smaller radius of curvature beta1 on the trailing row protrusions 143. Leading base 151 and protrusions 141 may also constrain the freedom of movement of the soft oral tissue so that protrusions 143 cannot dig freely into the soft oral tissue. In other words, protrusions 141 press against the soft oral tissue and limit the maximum contact between protrusions 143 and the soft oral tissue.

In some embodiments, leading base second surface 152c and trailing base first surface 154b form parallel planes. In other embodiments, leading base second surface 152c and trailing base first surface 154b may not form parallel planes. For example, leading row protrusion second contact edge 142e may not be orthogonal, trailing row protrusion first contact edge 144*d* may not be orthogonal, leading row protrusion second surface 142*b* may not be 180 degree continuous with leading base second surface 152*c*, or the trailing row protrusion first surface 144*a* may not be 180 degree continuous with trailing base first surface 154*b*.

Figure 4:
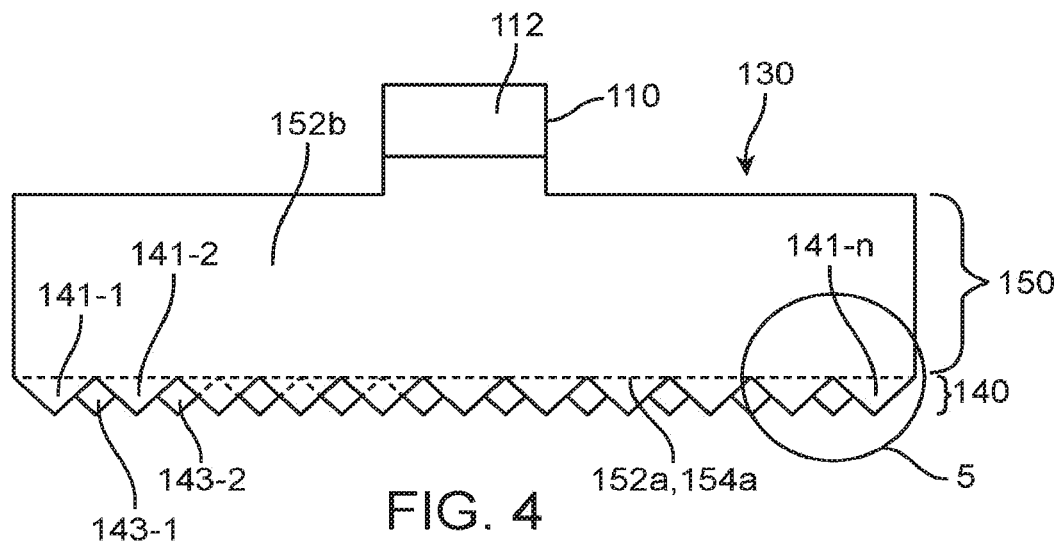
FIG. 4 illustrates a back view of an oral care implement according to an embodiment.

FIG. 4 illustrates a back view of tongue cleaner 100. Leading row protrusions 141 and trailing row protrusions 143 may have a serrated triangular saw-tooth-like shape with a free end of protrusions 141 and 143 forming an apex of a triangle. Protrusions 141 and 143 may be substantially angular, thus creating zigzagging corrugations. The angle of the tip of protrusions 141 and 143 and the angle between protrusions 141 and 143 may be about 90 degrees. Alternatively, the angle of the tip and/or the angle between protrusions may be greater than or less than 90 degrees. Protrusions 141 and 143 may also be rounded, scalloped, curved, or any other suitable shape, or a combination of different shapes. A suitable protrusion shape is any shape that enables the protrusion to loosen debris from the user's soft oral tissue. Protrusions 141 and 143 may be individual bumps or nubs (e.g., conical shaped) that project from leading base 151 or trailing base 153, respectively.

Figure 5:
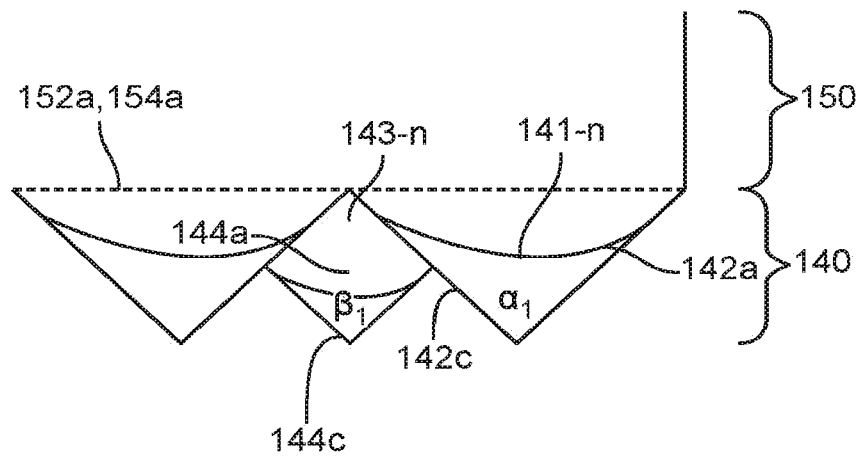
FIG. 5 illustrates a detail back view of the oral care implement of FIG. 4.

One or more trailing row protrusions 143 may be offset or misaligned from one or more of leading row protrusions 141 such that when viewed along the longitudinal axis L (i.e., down the handle), one or more trailing row protrusions 143 are visible between leading row protrusions 141. For example, each protrusion 141 of the leading base 151 may be centered between adjacent protrusions 143 of trailing base 153. FIG. 5 illustrates a detailed view of leading row protrusions 141 and trailing row protrusions 143. Alternatively, in some embodiments, one or more trailing row protrusions 143 may be situated directly behind one or more leading row protrusions 141 such that when viewed along the longitudinal axis L, one or more trailing row protrusions 143 are not visible. When protrusions 141 are offset from protrusions 143, protrusions 141 and 143 are able to clean different portions of the soft oral tissue. For example, protrusions 141 of leading base 151 may clean portions of the user's tongue and protrusions 143 of trailing base 153 may clean portions of the user's tongue that were not cleaned by leading base 151.

Figure 6:
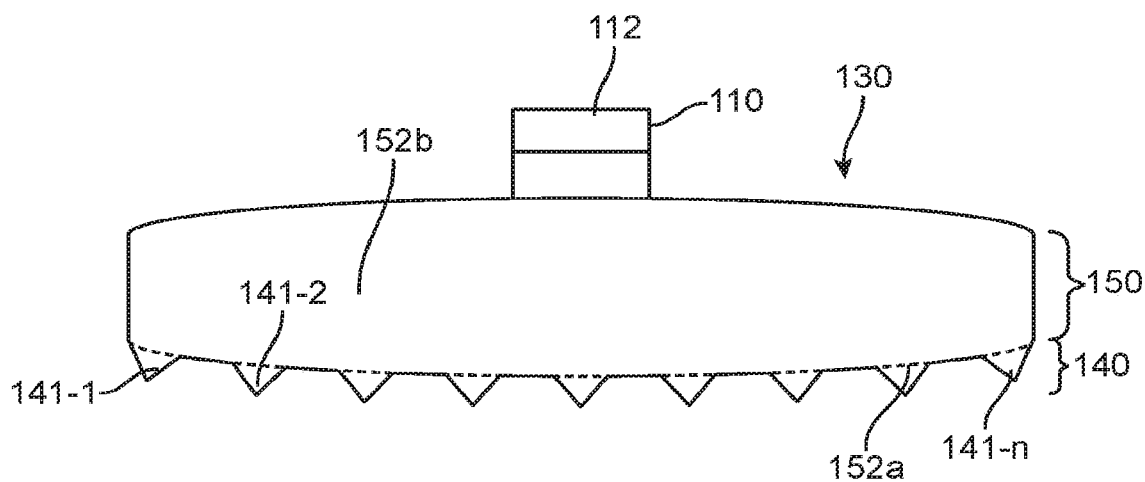
FIG. 6 illustrates a back view of an oral care implement according to an embodiment.

FIG. 6 illustrates a back view of exemplary embodiment of tissue cleanser 130, in which the bottom surface of collecting bases 151 and 153 of collecting region 150 may be formed with a convex curve. Accordingly, protrusions 141 in the center may be lower or extend further from the handle than protrusions 141 on the periphery of leading base 151. FIG. 7B illustrates a side view of collecting region 150 with a bottom surface with a convex curve. Protrusions 141 and 143 in the center extend further from the handle than protrusions 141 and 143 on the periphery of leading bases 151 and 153. The curvature of bases 151 and 153 helps the tongue readily adapt to the curvature of bases 151 and 153 when user applies pressure with tissue cleanser 130, which enables protrusions to more effectively clean the user's tongue. FIG. 6 further illustrates that protrusions 141 may be spaced apart from each other along leading base 151.

Protrusions 141 and 143 of cleaning region 140 may have a height and a width that is configured to enable protrusions 141 and 143 to loosen debris from the oral tissue and enable collecting region 150 to remove and collect the loosened debris from cleaning region 140. For example, protrusions 141 and 143 may be at least 0.8 mm wide as measured along traverse axes T1 and T2. The height of protrusions 141 and 143 may be, for example, at least 0.5 mm. Protrusions 141 and 143 may have spacing between the adjacent protrusions 141 and 143 along collecting bases 151 and 153 to improve collection of debris by collecting bases 151 and 153. For example, adjacent protrusions 141 and 143 may be between 0 mm and 3 mm. The soft tissue in the mouth is typically not smooth and contains many different surfaces and shapes. For example, the tongue contains four different types of lingual papillae: circumvallate papillae, foliate papillae, fingiform papillae, and filiform papillae. Each of these papillae have different shapes, heights, widths, and spacing on the tongue. The location of the vascular capillaries and the nerve receptors (e.g., nociceptor, mechanoreceptor, baroreceptors, etc.) vary from location to location of the soft oral tissue. Protrusions 141 and 143 may have an interpapillary shape that ideally fits between the papillae to remove debris and clean the tongue, and minimally triggering pain nociceptors. For example, the angle of the tip of the protrusions, the angle between protrusions, the height of the protrusions, the width of the protrusions and the spacing between adjacent protrusions enables the protrusions to fit between the lingual papillae of a user's tongue and loosen and collect debris on the soft oral tissue.

The height, width, and spacing between two adjacent protrusions on a row may vary, offering the user a variety of different protrusion sizes on the same row. In the same manner, the height, width, and spacing between two adjacent protrusions may vary between leading row protrusions 141 and trailing row protrusions 143. The number of protrusions found on first collecting base 151 may differ from the number of protrusions on the second collecting base 153.

Tissue cleanser 130 may have a "softness" that is generated by varying various variables. As illustrated in FIG. 2, the softness variable may include a distance d1, which is the closest distance between leading row protrusion second contact edge 142*e* and the trailing row protrusion first surface 144*a*, the radius of curvatures alpha1, alpha2, beta1, beta2, the material and finish used to construct the leading row protrusions 141, and the material and finish used to construct the trailing row protrusions 143. One or more softness variables may be modified to create an oral care implement with a desired "softness" to fit the user's individual preference. Distance d1 may be between 500 microns and 5000 microns, alpha1 may be between 100 microns and 500 microns, alpha2/beta1/beta2 are all less than or equal to 500 microns, and the material is a polymer with a Shore hardness between Shore A 0 and Shore A 90. In some embodiments, the distance d1 may be greater than 5000 microns. Increasing the radius of curvature alpha1 increases the softness of the implement. Increasing the radius of curvatures alpha2, beta1, and beta2 also increases the softness of the implement. Although depending on the other variables, in most instances, decreasing the distance d1 increases the softness. One skilled in the art would appreciate that these values are one of many possible softness variable combinations, and that other variable combinations are understood to be part of this disclosure because these values are adjusted to target the cleaning of the desired oral tissue, the preferences of the user, and the species of the user (e.g. human, feline, canine, equine, bovine, porcine, elephantidae, etc.). The softness variable may also vary based on the different shapes, heights, widths, and spacing of the differ papillae. The softness variable may vary from point to point along the length of the leading row protrusions 141, and may vary from point to point along the length of the trailing row protrusions 143.

As the softness variables may be varied to the many different applications of the disclosed oral care implement, handle 110, intermediary region 120, and tissue cleanser 130 may be adapted as well. For example, in some embodiments for non-human application, handle 110 and intermediary region 120 may be extended or shortened to allow for a sufficient and comfortable reach of the oral tissue in a desired animal. Tissue cleanser 130 may be flattened into a paddle shape, see FIG. 10. The paddle shaped tissue cleanser 130 may have a first face and a second face opposite the first face and collecting bases 151 and 153 may extend from the first face. In some embodiments, the flat paddle shape may be curved. In other embodiments, tissue cleanser 130 may also be rounded into a cylindrical, spherical, torus, conic, or other shapes, with the protrusions covering at least a portion of the surface. For example, a cylindrical tissue cleanser may have protrusions along an outer surface of the cylinder.

Tongue cleaner 100 may further include a channel 156 for collecting the loosened debris from collecting region 150 as the user guides tongue cleaner 100 over the surface of the tongue. Channel 156 may be disposed between adjacent bases 151 and 153. Alternatively, if tongue cleaner 100 includes multiple bases, tongue cleaner 100 may include multiple channels disposed between adjacent bases. FIG. 2 illustrates channel 156 connecting leading base second surface 152c and trailing base first surface 154b. The cross-section of channel 156 may have a variety of different shapes, such as, semi-circular, triangular, polygon, and the like. Channel 156 may extend the width of tissue cleanser 130 and may be disposed within tissue cleanser 130. The user may clean out the collected debris from the channel 156 between uses of tongue cleaner 100.

Channel 156 is illustrated as straight in FIG. 3 along traverse axis T3; however, channel 156 may have a variety of different shapes, such as curved, angled, and the like. Channel 156 may have varying widths along the width of tissue cleanser 130. The curvature and shape of channel 156 affects the way debris is collected and dispelled during use of tongue cleaner 100. For example, if channel 156 has a curve that is convex relative to handle 110, tissue cleanser 130 may dispel more of the debris from periphery 158 of channel 156 when tissue cleanser 130 is moved in the direction of handle 110. By dispelling the debris, trailing row protrusions 143 are more effective at cleaning the tongue. If channel 156 has a general curvature that is concave relative to handle 110, tissue cleanser 130 may retain more of the debris within the groove, and the debris may be removed from tongue cleaner 100 when tongue cleaner 100 is rinsed or washed. The depth of channel 156 may be non-uniform such that it varies along traverse axis T3 of tissue cleanser 130 and is deeper near periphery 158 of channel 156 and shallower near the center or vice versa.

Figure 7A:
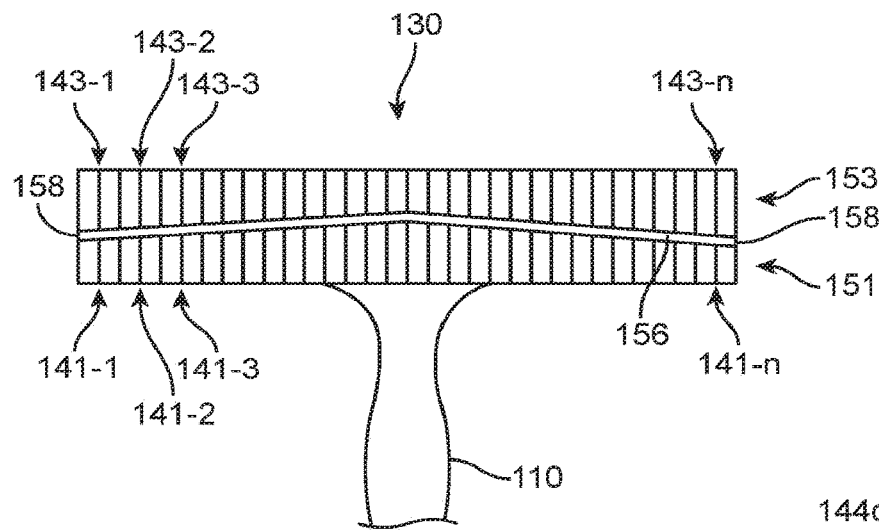
FIG. 7A illustrates a bottom view of an oral care implement according to an embodiment.
Figure 7B:
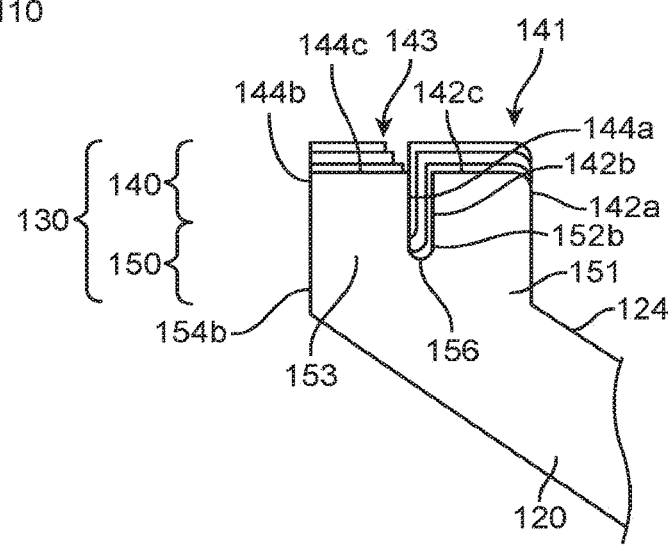
FIG. 7B illustrates a side view of an oral care implement according to an embodiment.
Figure 8:
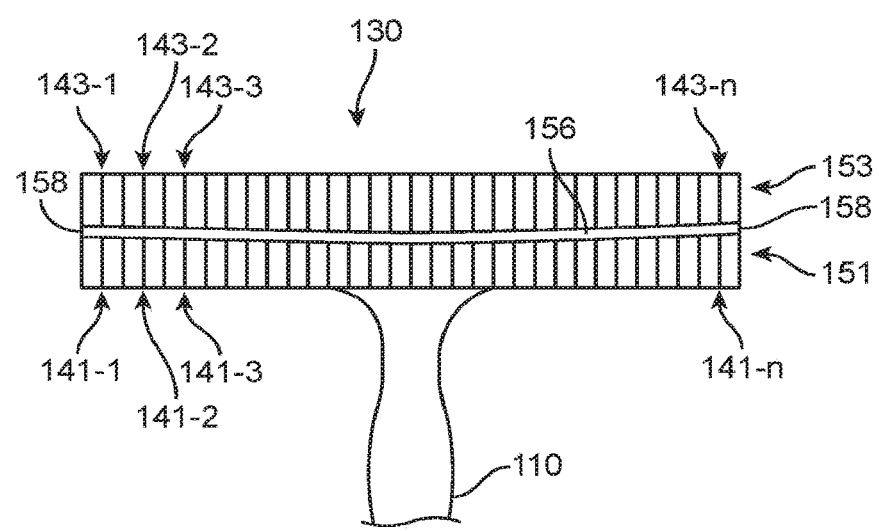
FIG. 8 illustrates a bottom view of an oral care implement according to an embodiment.

FIG. 7A illustrates a bottom view of an exemplary embodiment of tongue cleaner 100 with an angled channel 156. The shape and size (e.g., height, width, length) of protrusions 141 and 143 may vary based on the shape of angled channel 156. For example, as illustrated in a side view of tissue cleanser 130 in FIG. 7B, protrusions 141 may increase in length (i.e., length of tooth in the longitudinal direction L of handle 110) from the ends of leading row protrusions 141 to the center of leading row protrusions 141. Conversely, each protrusion 143 of trailing row protrusions 143 may decrease in length in longitudinal axis L direction from the ends of trailing row protrusions 143 to the center of trailing row protrusions 143. Protrusions 141 and 143 may be aligned, as illustrated in FIG. 7A, or protrusions 141 and 143 may be offset. FIG. 8 illustrates a bottom view of an exemplary embodiment of tongue cleaner 100 with curved channel 156. Similar to FIG. 7A, each protrusion 141 of first collecting base 151 may decrease in length in the longitudinal axis L direction from the ends of leading row protrusions 141 to the center of leading row protrusions 141. Conversely, protrusions 143 of second collecting base 153 may increase in length from the ends of trailing row protrusions 143 to the center of trailing row protrusions 143.

Figure 9:
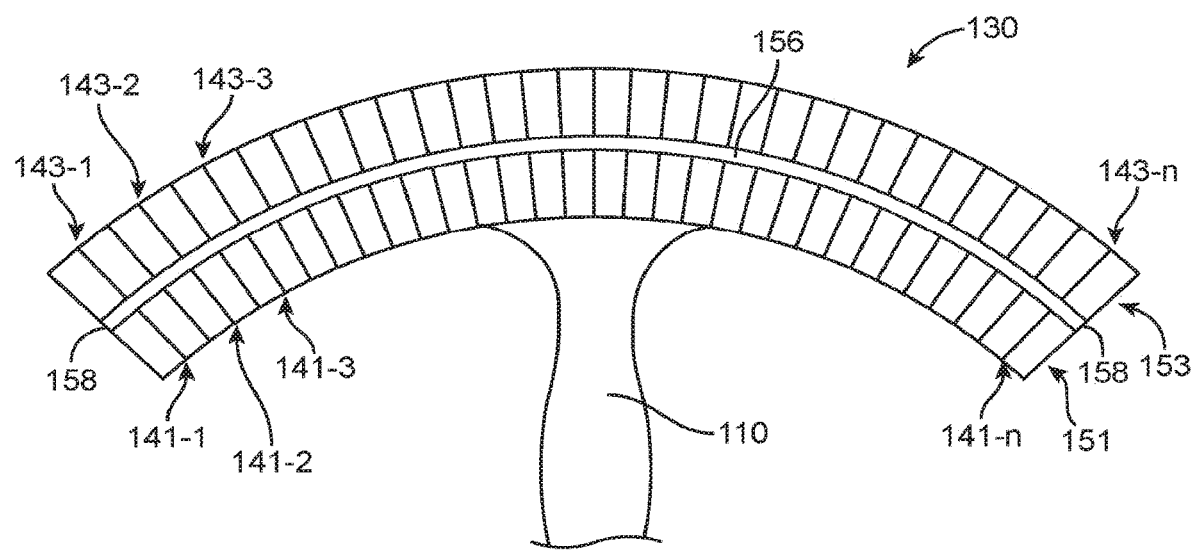
FIG. 9 illustrates a bottom view of an oral care implement with curved collecting bases according to an embodiment.

FIG. 9 illustrates a bottom view of an exemplary embodiment of tongue cleaner 100 with a curved tissue cleanser 130. Collecting bases 151 and 153 of tissue cleanser 130 may be curved and extend away from handle 110 in opposing directions. Collecting bases 151 and 153 may have a channel 156 that is curved and disposed between collecting bases 151 and 153.

Figure 10:
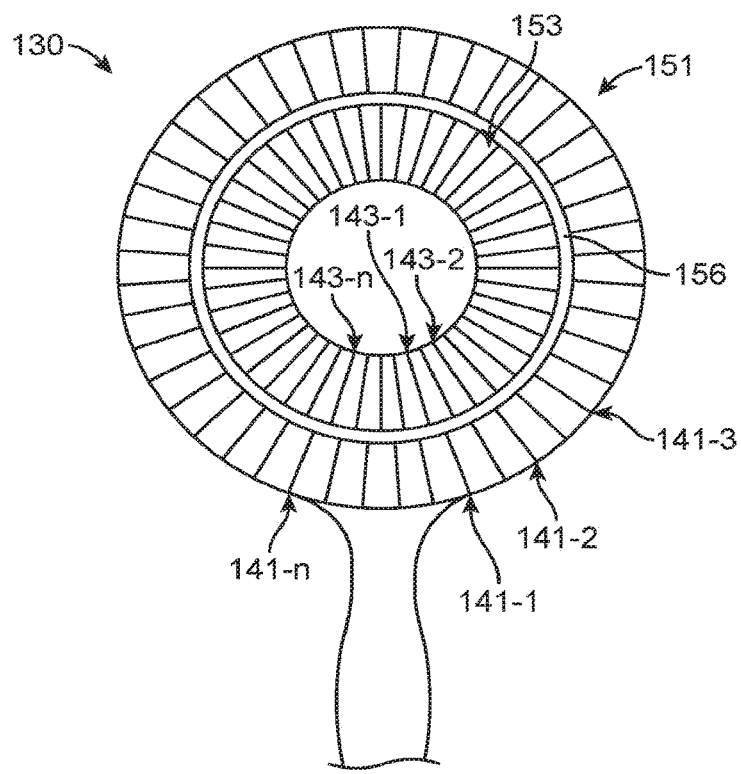
FIG. 10 illustrates a bottom view of an oral care implement with concentric collecting bases according to an embodiment.

FIG. 10 illustrates a bottom view of an exemplary embodiment of a tongue cleaner 100 with tissue cleanser 130. Tissue cleanser 130 includes collecting bases 151 and 153 that are formed in concentric closed curves, such as circles, ovals, quadrilateral, triangles and the like. For example, FIG. 10 illustrates leading base 151 as an outer circle and trailing base 153 as an inner circle. Protrusions 141 of leading base 151 may have a greater radius of curvature than the protrusions 143 of trailing base 153. Accordingly, the user may move tongue cleaner 100 in any direction (i.e., forward, backward, left, right, angled, and the like) and keep the leading base 151 in front of trailing base 153. Channel 156 may be a similar shape to the closed curved and may be disposed between collecting bases 151 and 153. For example, channel 156 is FIG. 10 is circular.

Figure 11:
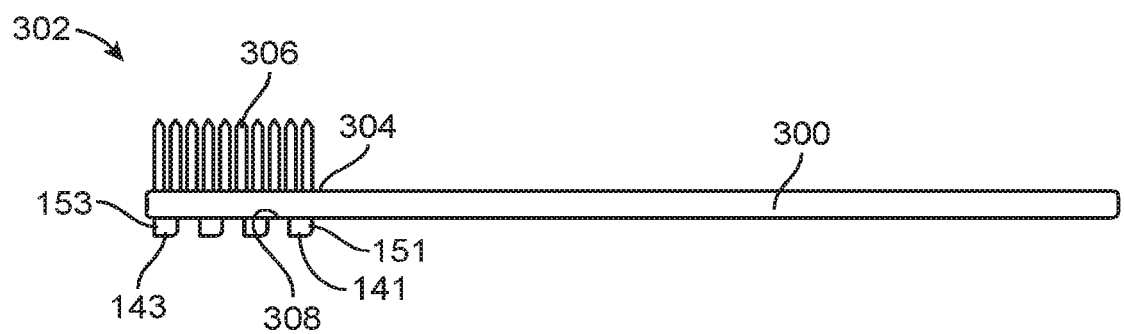
FIG. 11 illustrates a side view of an oral care implement with bristles and a tissue cleaner according to an embodiment.

FIG. 11 illustrates a toothbrush 300 with tissue cleanser 130 disposed on the back side of a toothbrush head 302, thus enabling the user to brush their teeth and clean their tongue with the same oral implement. A front face 304 of toothbrush head 302 may have a plurality of bristles 306 for cleaning the user's teeth. A back face 308 may have collecting bases 151, 153, etc., that project from back side 308 of toothbrush head 302, each collecting base 151, 153, etc. has a plurality of protrusions. Leading row protrusions 141 and trailing row protrusions 143 may project from collecting bases 151, 153, etc., and may be the same width as toothbrush head 302.

Figure 12:
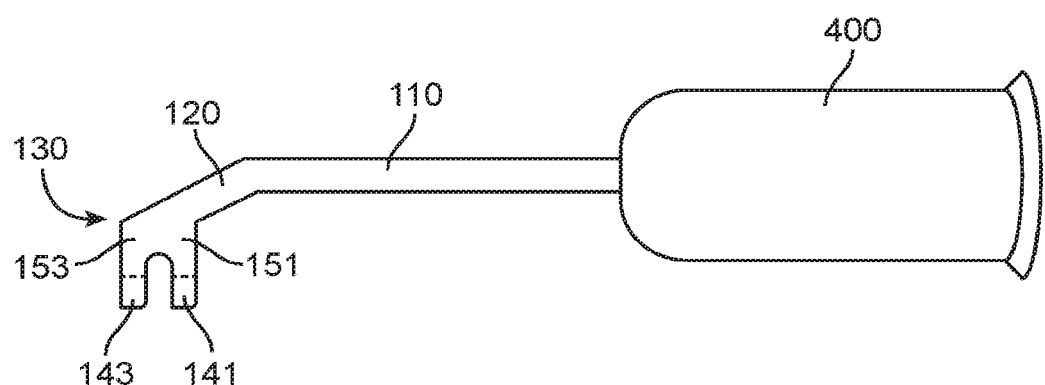
FIG. 12 illustrates a side view of an oral care implement with a tissue cleanser coupled to a sonic electric vessel according to an embodiment.

FIG. 12 illustrates tissue cleanser 130 coupled to a vessel 400 which converts electrical energy into vibrations or sonic impulses, such as a sonic electric toothbrush body. Vessel 400 may impart vibrations or sonic impulses to tissue cleanser 130. Protrusions 141 and 143 may impart the received impulses/vibrations to the soft oral tissue, loosening and facilitating removal of the oral debris. Each protrusion 141 and 143 may serve as a wave origination point for the vibration or impulse. Waves from multiple protrusions can be used to form constructive and destructive interference wave patterns, further facilitating the debris removal. The spacing and size of protrusions 141 and 143, and the wave forms can be varied to achieve the desired interference pattern.

Tissue cleanser 130 may also be positively or negatively charged during use to further improve cleaning of the user's tongue. The mouth and tongue may contain many charged particles or solutions. Dental tartar has a positive charge since dental tartar is comprised mostly of calcium phosphate salt. Dental microbial flora is acidic and produces a considerable amount of acidic debris that carries a positive charge. Accordingly, if tissue cleanser 130 is negatively charged, tissue cleanser 130 may be able to collect the debris from the user's mouth more effectively. Alternatively, protrusions 141 and 143 may have different electric potentials or different portions of protrusions 141 and 143 may have different electric potentials. Different electric potentials may include opposite electric charges. For example, leading row protrusion contact surface 142c may have a positive charge and leading row protrusion first surface 142a and leading row protrusion second surface 142b may have a negative charge to help move debris away from the tongue. The charges may differ in intensity for the various surfaces in order to achieve a reliable cleaning surface.

Tissue cleanser may be charged in a variety of different manners. For example, tongue cleaner 100 may include a power source 200 (See FIG. 1) and electrical wires impregnated within tongue cleaner 100 to create an electric potential. Alternatively, the material used for tissue cleanser 130 may have an electrical potential. For example, food grade polyelectrolytes with an electrical potential may be used to compound a material, such as a plastic, for tissue cleanser 130. This compounded plastic may carry or generate an electric potential on the plastic without the need for a power source. Examples of food grade polyelectrolytes include pectin, carrageenan, alginates, and carboxymethyl cellulose.

In some embodiments, tissue cleanser 130 may include sensors to detect the presence of bacteria and oral debris, a user's temperature, the pressure of tissue cleanser 130 against soft oral tissue, and so forth. Properties of the material used in the fabrication of tissue cleanser 130 may include thermochromic properties, halochromic properties, piezochromic properties, and so forth and may indicate the presence of a certain criteria based on a predetermined threshold. In the presence of varying pH, the material may change colors or transparency indicating the presence of bacteria. For example, the material may contain a leuco dye that changes from a colorless form to a colored form based on pH. Since debris is generally acidic, the pH change would generate a color change in the material. Examples of food safe halochromism materials include anthocyanin, hydrangeas, and litmus, all of which are found in edible plants.

In some embodiments, one or more regions of tissue cleanser 130 may be coated with a chromic material. In embodiments where tissue cleanser 130 is disposed on toothbrush 300, bristles 306 or a portion of bristles 306 may be constructed to exhibit detection properties. For example, bristles 306 may be chemically compounded to include halochromic dyes. Alternatively, bristles 306 may include smart polymers that bend in the presence of pH changes or organic materials, thereby imparting feedback of the sensing by bending.

In another application, sensors may be used to detect the user's degree of halitosis, based on the pH of the user's breadth. In some embodiments, halitosis detection can be achieved with gasochromic polymers that detect compounds such as hydrogen sulfide and dimethyl sulfide.

In some embodiments, tissue cleanser 130 may be fabricated from a material or substance that exhibits thermochromic properties and may be used to detect the user's oral temperature and thus alert the user of a fever. This can be particularly useful in embodiments configured for animal use where it is difficult to take the temperature of the animal. Examples of a non-toxic thermochromic includes biopolymer poly(lactic acid) (PLA), a natural dye of the anthocyanidine class, a gallate derivative and a fatty acid, which is discussed in "First example of a non-toxic thermochromic polymer material—based on a novel mechanism" J. Mater. Chem. C., 2103, 1, 2811, which is hereby incorporated herein by reference in its entirety.

In some embodiments, tissue cleanser 130 material exhibit piezochromic properties. The material may be used to construct tissue cleanser 130 contact surface, toothbrush bristles 306, or handle 110. The material may change colors depending on the pressure applied to tissue cleanser 130, thereby imparting feedback to the user concerning the amount of pressure being applied (e.g., whether the user is pressing too hard, too soft, or imparting the correct amount of pressure). This is especially important for toothbrush 300 because some users apply too much pressure when brushing their teeth. The piezochromic enabled toothbrush or tissue cleanser 130 may indicate to the user whether the correct pressure is being applied. In some embodiments, tissue cleanser 130 is configured for use with an animal, it may provide feedback to the user about the correct amount of pressure to use so as to not injure or cause pain to the animal. It will be appreciated by those skilled that various techniques may be employed to compound or coat chromic polymers into/onto tissue cleanser 130 and toothbrush 300, and is considered part of this disclosure.

In another embodiment, leading row protrusions 141 and trailing row protrusions 143 may be coated with a softer polymer than the material used for collecting bases 151 and 153 for user's comfort.

In some embodiments, tissue cleanser 130 may be flavored to order to incentivize children or animals to use tongue cleaner 100. Tissue cleanser 130 may be fabricated from a flavored polymer, coated with a flavored polymer or substance. Alternatively, a flavored gel or insert may be applied to tissue cleanser 130 before each use.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An oral care implement comprising:
   a handle;
   a plurality of collecting bases coupled to the handle;
   a plurality of protrusions extending from each collecting base and away from the longitudinal axis of the handle, each protrusion having a radius of curvature less than 500 microns; and
   a collecting depression disposed between an adjacent pair of collecting bases for collecting debris dislodged by the protrusions,
   wherein the protrusions of one collecting base are offset from the protrusions of another collecting base such that when viewed along the longitudinal axis of the handle, protrusions on one collecting base are visible between protrusions on another collecting base.

2. The oral care implement of claim 1, wherein each protrusion has a single radius of curvature in the longitudinal direction, and
   wherein the radius of curvature of each of the protrusions on one of the collecting bases is greater than the radius of curvature of each of the protrusions on another collecting base.

3. The oral care implement of claim 1, wherein the plurality of collecting bases are formed in rows that extend perpendicular to the longitudinal direction of the handle.

4. The oral care implement of claim 3, wherein the plurality of collecting bases are formed in rows that curve away from the handle in opposing directions.

5. The oral care implement of claim 3, wherein a bottom surface of each collecting base has a convex curve such that protrusions at the center of the collecting base are lower than protrusions at the periphery of the collecting base.

6. The oral care implement of claim 1, wherein the plurality of collecting bases are formed in concentric circles.

7. The oral care implement of claim 1, wherein each of the protrusions have a substantially triangular saw-tooth shape, and wherein a free end of each of the protrusions forms the apex of a triangle.

8. The oral care implement of claim 1,
wherein the collecting depression is formed as a channel.

9. The oral care implement of claim 1, wherein the depth of the collecting depression varies along an axis of the collecting depression.

10. The oral care implement of claim 9, wherein the depth of the collecting depression is different near a periphery of the collecting depression than the depth of the collecting depression is near a center of the collecting depression.

11. The oral care implement of claim 1, wherein the height and width of the protrusions enables them to fit between the lingual papillae of a user's tongue.

12. The oral care implement of claim 1, further comprising a head that has a flat paddle shape, and the collecting bases extend from the head.

13. The oral care implement of claim 1, wherein the protrusions are electronically charged.

14. The oral care implement of claim 13, wherein the protrusions are positively charged and the collecting bases are negatively charged.

15. The oral care implement of claim 1, wherein the collecting bases and protrusions are fabricated from a material containing a substance for measuring the pH in a user's mouth.

16. The oral care implement of claim 1, wherein the collecting bases and protrusions are fabricated from a material containing a substance for measuring the user's temperature.

17. The oral care implement of claim 1, wherein the protrusions are coated with a flavored substance.

18. The oral care implement of claim 1, wherein the handle is attachable to a vibration creation device for causing the protrusions to vibrate.

19. A toothbrush comprising:
a handle;
a head connected to the handle, the head having a first face and a second face opposite to the first face;
a plurality of bristles extending from the first face of the head; and
a plurality of collecting bases projecting from the second face of the head and extending the entire width of the second face; and
a plurality of protrusions extending from each collecting base,
wherein a bottom surface of each collecting base has a convex curve such that protrusions at the center of the collecting base are lower than protrusions at the periphery of the collecting base, and
wherein a collecting depression is disposed between an adjacent pair of collecting bases.

20. The toothbrush of claim 19, wherein a radius of curvature of the protrusions on a collecting base is greater than a radius of curvature of the protrusions on another collecting base.

* * * * *